United States Patent [19]

Iles

[11] Patent Number: 5,372,786
[45] Date of Patent: Dec. 13, 1994

[54] METHOD OF HOLDING A SAMPLE CONTAINER

[75] Inventor: Kenneth E. Iles, Los Altos, Calif.

[73] Assignee: Abbott Laboratories, Abbott Park, Ill.

[21] Appl. No.: 163,618

[22] Filed: Dec. 8, 1993

Related U.S. Application Data

[63] Continuation-in-part of Ser. No. 86,744, Jul. 2, 1993, Pat. No. 5,306,469.

[51] Int. Cl.⁵ ................................................. B01L 9/06
[52] U.S. Cl. ........................................ 422/104; 422/99; 422/100; 422/102; 436/809; 436/810; 206/562; 206/563; 211/74; 435/809
[58] Field of Search .............. 422/99, 100, 102, 104; 435/296, 298, 809; 436/809, 810; 206/443, 446, 522, 562, 563; 211/74, 89; 277/34.3, 34.6

[56] References Cited

U.S. PATENT DOCUMENTS

| | | | |
|---|---|---|---|
| 2,630,233 | 3/1953 | Kircher | 211/74 |
| 3,456,783 | 7/1969 | Clark | 206/65 |
| 3,593,873 | 7/1971 | Vonk | 220/21 |
| 3,819,081 | 6/1974 | Runte | 206/446 X |
| 4,073,620 | 2/1978 | Gray et al. | 23/253 R |
| 4,180,272 | 12/1979 | Heitz | 277/28 |
| 4,306,665 | 12/1981 | Hickey | 277/34.3 X |
| 4,510,119 | 4/1985 | Hevey | 422/71 |
| 4,874,102 | 10/1989 | Jessop et al. | 422/102 X |
| 4,913,286 | 4/1990 | Tate | 206/329 |
| 4,932,533 | 6/1990 | Collier | 206/569 |
| 4,963,493 | 10/1990 | Daftsios | 435/287 |
| 5,096,078 | 3/1992 | McQueeny | 206/522 X |
| 5,102,150 | 4/1992 | Kahn | 277/34.3 |
| 5,121,150 | 4/1992 | Kahn | 277/34.3 |

Primary Examiner—James C. Housel
Assistant Examiner—Harold Y. Pyon
Attorney, Agent, or Firm—Mark C. Bach; Richard D. Schmidt

[57] ABSTRACT

A method of holding a container with a container holder comprises the following steps. The container is received within a bore on the container holder, and a fluid is conveyed through a fluid passage operatively connected with a flexible element within the bore such that the flexible element engages the container to retain the container within the bore.

11 Claims, 5 Drawing Sheets

METHOD OF HOLDING A SAMPLE CONTAINER

REFERENCE TO RELATED APPLICATIONS

This application is a continuation-in-part of U.S. Ser. No. 08/086,744 filed Jul. 2, 1993, now U.S. Pat. No. 5,306,469, the disclosure of which is specifically incorporated herein by reference.

FIELD OF THE INVENTION

The present invention relates to a method of holding a container in an automated analytic system. More particularly, the invention relates to a method of operating a holder for gripping and holding sample containers as the containers are transported, inverted to mix or agitate their contents or otherwise moved.

BACKGROUND OF THE INVENTION

Holders now used in the field of automated clinical analysis may employ methods using mechanical grip devices for gripping sample containers after the holders are positioned over the upper portions of the containers. In addition to often being complex and hard to clean, some mechanical grippers and the associated methods of use have other disadvantages. These grippers may not readily accommodate sample containers having different diameters or varying cap configurations. Furthermore, in the event of a power or other failure, a mechanical gripper may lose its grip on the container. The containers may be dropped, thereby spilling their contents.

A further disadvantage may be present when a holder with a mechanical grip device is employed in a mixer or shaker device which inverts the holder and the containers in order to mix the contents of the containers. Since, according to some prior art methods, a mechanical gripper often grips the upper portion of the sample containers but not their caps, a cap may separate from a container during the inverting process thereby spilling the container contents. Therefore, it is desirable to provide an improved method for holding a sample container.

SUMMARY OF THE INVENTION

A method of holding a sample container that contains a sample with a sample container holder comprises the following steps. A sample container holder is provided comprising a body having at least one bore in which a container is received, first and second tubular elements of different inner and outer diameters disposed within the at least one bore, the first tubular element being rigid and having an inner diameter larger than the outer diameter of the second tubular element, the second tubular element being flexible and disposed within the first tubular element with first and second ends of the second tubular element being folded back over first and second ends of the first tubular element so as to form a substantially sealed chamber between the first and second tubular elements, and the first tubular element and the body having openings therein comprising a fluid passage. A container is received within the at least one bore in the body of the sample container holder. A pressure is introduced through the fluid passage to the chamber to change the inner diameter of the second tubular element such that the container is held in the bore by the second tubular element.

In other words, the method of holding a container with a container holder comprises the following steps. The container is received within a bore on the container holder, and a fluid is conveyed through a fluid passage operatively connected with a flexible element within the bore such that the flexible element engages the container to retain the container within the bore.

DETAILED DESCRIPTION OF PREFERRED EMBODIMENTS

For the sake of clarity of understanding, embodiments of the present invention will be discussed in detail with respect to their employments with a container that holds a sample. However, it is to be noted that the embodiments of the invention can be utilized with containers holding other things or with types of vessels different from those described and illustrated in the Figures. Additionally, for the sake of clarity, the embodiments of the invention are illustrated in the Figures associated with a plurality, specifically four, containers. It is to be remembered that the embodiments of the invention may be used with any number of containers. Therefore, the gripper illustrated in FIGS. 9 and 10 may be the only gripper associated with the container holder. Alternatively, more than one gripper may be associated with a single container holder. All of these permutations are possible without departing from the scope of the present invention.

Figure 1:
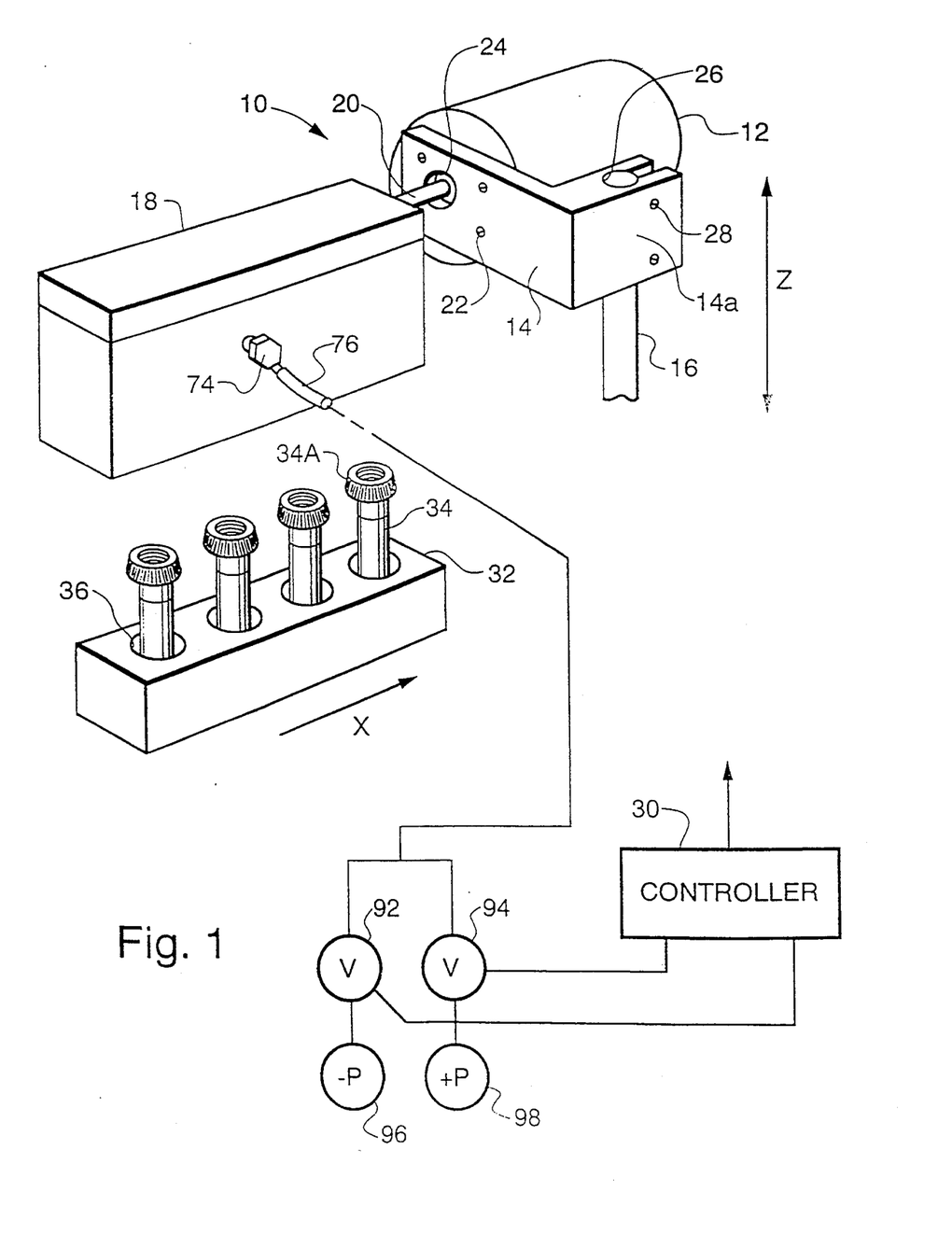
FIG. 1 is a schematic diagram of a prior art mixer device, modified to include a sample container holder which can perform a method according to the teachings of the present invention.

The structure of an exemplary embodiment of a container holder for executing a method according to an embodiment of the invention will be described first. FIG. 1 schematically illustrates a prior art mixer or shaker device including a sample container holder 18 constructed according to the teachings of the present invention. The mixer device has a head assembly 10 comprising a reversible stepper motor 12, an L-shaped clamp 14, and a vertically extending shaft 16. In the illustrated embodiment, the holder 18 is mounted on the shaft 20 of the stepper motor 12 so that the holder 18 may be rotated in substantially opposite directions through an angle, preferably measuring about 150°, as the motor 12 is energized.

The motor 12 is attached to clamp 14 by a plurality of fasteners 22. An aperture 24 is provided in the clamp 14 so that the motor shaft 20 may extend therethrough. The shaft 16 extends through an aperture 26 in a leg 14a of the clamp 14. The leg 14a is bifurcated from the aperture 26 to the edge of the leg 14a. Fasteners 28 are provided for securing the leg 14a to the shaft 16.

The head assembly 10 is movable in a Z direction, as shown in FIG. 1, by a conventional mechanism (not shown) which may be controlled by a controller 30 which may be microprocessor-based. The controller 30 also may control energization of stepper motor 12 to rotate the holder 18, and energization of a conventional conveyor mechanism (not shown) which conveys container carriers 32 in an X direction, as shown in FIG. 1, to a position adjacent the holder 18. Each container carrier 32 has at least one receptacle or recess 36 therein and supports one or more containers 34 having caps or closures 34a. The containers 34 may be pre-evacuated containers, test tubes or similar sample containers having caps or closures for preventing spillage of a sample contained therein.

In the illustrated embodiment, the head assembly 10 is moved to a raised position after which a carrier 32 is moved into position adjacent the holder 18. The head assembly 10 is then moved such that the caps 34a and portions of containers 34 enter the holder 18. The holder 18 is then actuated to grip the containers 34 and the head assembly 10 is raised until ends of the containers 34 are clear of the carrier 32. The stepper motor 12 is then actuated to rotate holder 18 and the containers 34 through an arc, preferably measuring about 150 degrees, after which the holder 18 is rotated back through an arc, which may be the same as the first-mentioned arc, until the containers 34 are again in a substantially vertical position. The arcuate rotation may be repeated one or more times as dictated by the controller 30.

In an exemplary embodiment, the rotation of the holder 18 and container 34, first in one direction and then another, can shake and mix the contents of the containers 34. After the mixing is completed, the head assembly 10 is moved to replace the containers 34 in the carrier 32. The holder 18 releases the containers 34 and the head assembly 10 is moved so that the holder 18 is offset from the containers 34. The conveyer mechanism is then actuated to move the carrier 32 from a position adjacent the holder 18 and to place another carrier 32 in its place. This completes one mixing cycle and the device is ready to repeat the mixing cycle using a new group of containers 34.

For the sake of simplicity, FIG. 1 shows a carrier 32 having only one row of container-receiving receptacles 36. However, carriers having more than one row of receptacles may be used. In the latter case, the controller 30 preferably is programmed to index the conveyor mechanism which transports the carriers by the distance between centers of adjacent rows of receptacles after each mixing cycle and another carrier is moved into position only after all the samples in a preceding carrier have been mixed.

Figure 2:
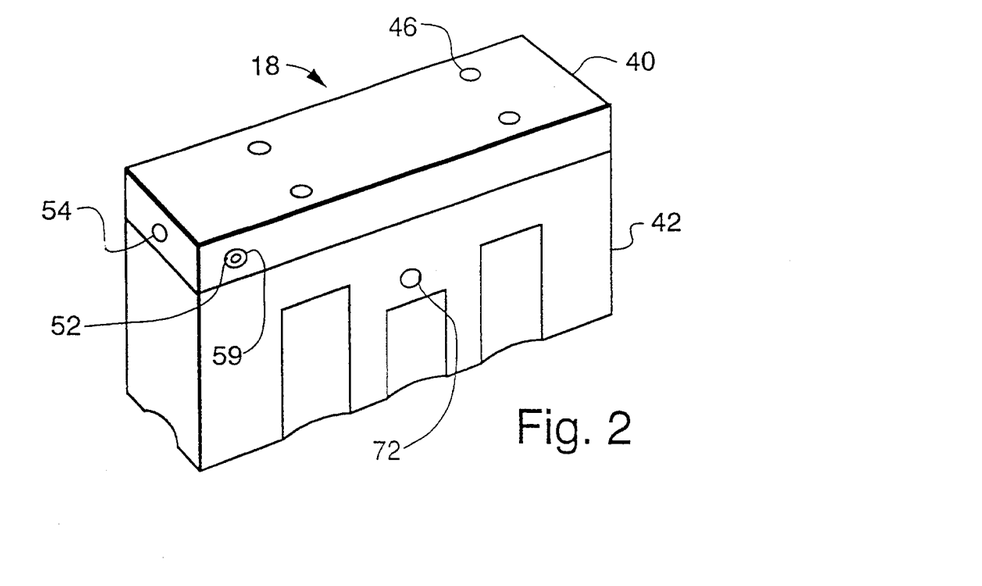
FIG. 2 is a perspective view of the holder of FIG. 1.
Figure 3:
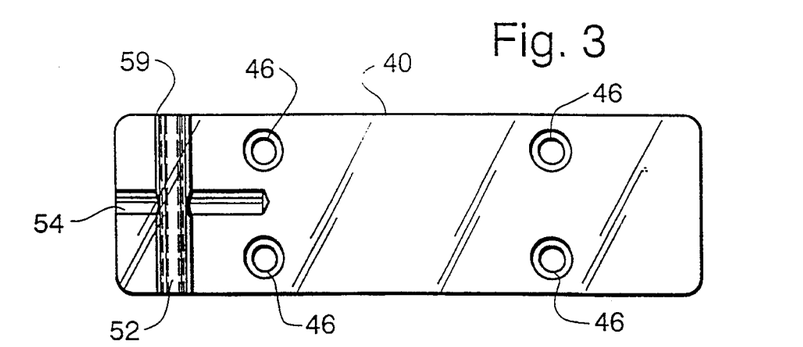
FIG. 3 is a top view of the holder cap.
Figure 5:
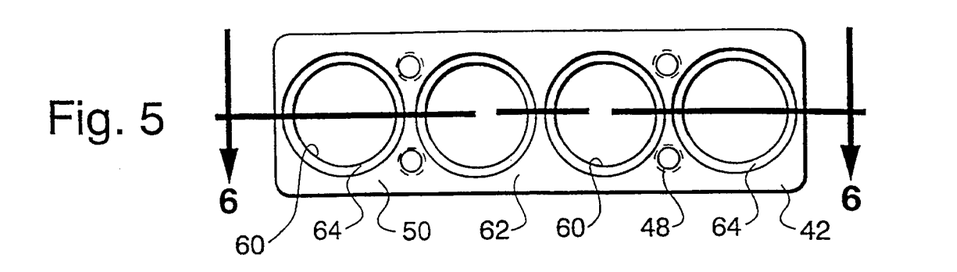
FIG. 5 is a top view of the holder body.
Figure 6:
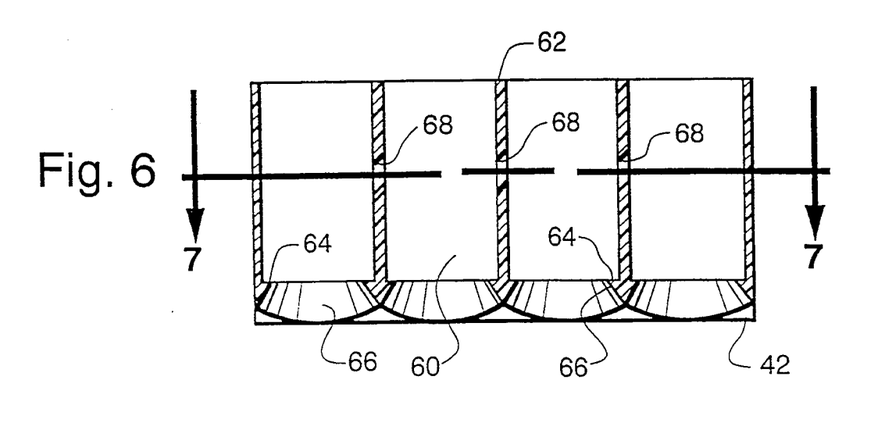
FIG. 6 is a sectional view of the holder body taken along the line 6—6 of FIG. 5.
Figure 7:
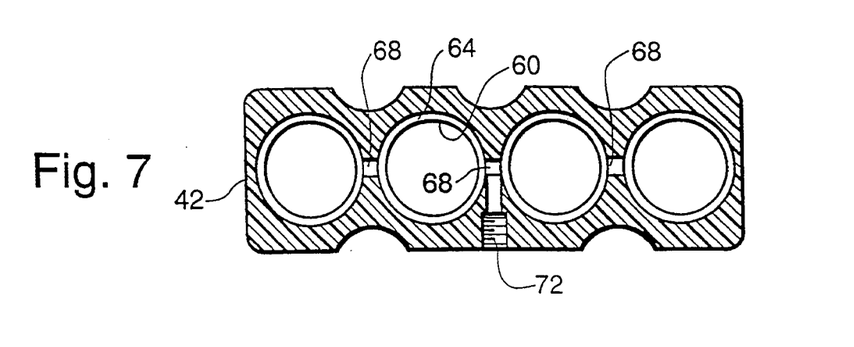
FIG. 7 is a sectional view of the holder body taken along the line 7—7 of FIG. 6.
Figure 8:
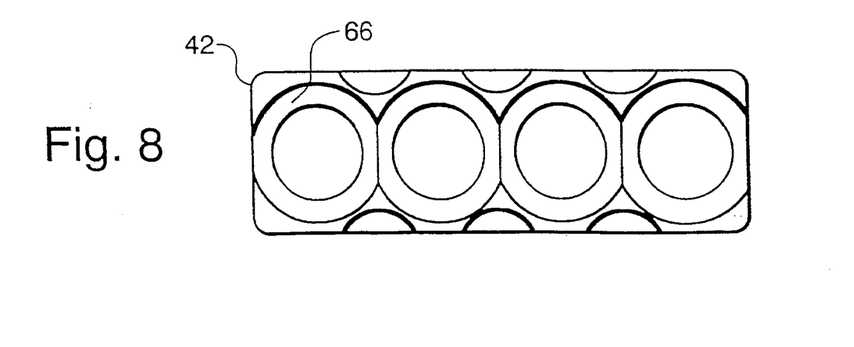
FIG. 8 is a bottom view of the holder body.

In an exemplary embodiment, the holder 18 utilizes fluid actuated grippers for gripping and holding the containers 32 as they are moved and/or shaken. As shown in FIG. 2, the holder 18 comprises a cap or cover 40 and a body 42. The cap 40 has at least one aperture 46 extending through it. The apertures 46 are counter-bored from one side as shown in FIG. 3. A corresponding number of apertures 48 (FIG. 5), preferably threaded, are provided in the surface 50 of body 42. The cap 40 is secured to body 42 by fasteners (not shown) which extend through apertures 46 and engage mating members, such as threads, in apertures 48.

The cap 40 is provided with at least one bore 59 (FIG. 3) extending from one side of the cap 40 to the opposing side. A metal insert 52 (FIG. 2) is placed and preferably press-fitted into bore 59. The insert 52 is preferably internally threaded from both sides. At least one bore 54 is drilled into one end of cap 40 and through insert 52. The shaft 20 of stepper motor 12 is inserted into bore 54. Fasteners (not shown) are inserted into both ends of insert 52 and tightened against the shaft 20 thereby securing cap 40 and body 42 to the shaft 20.

Figure 4:
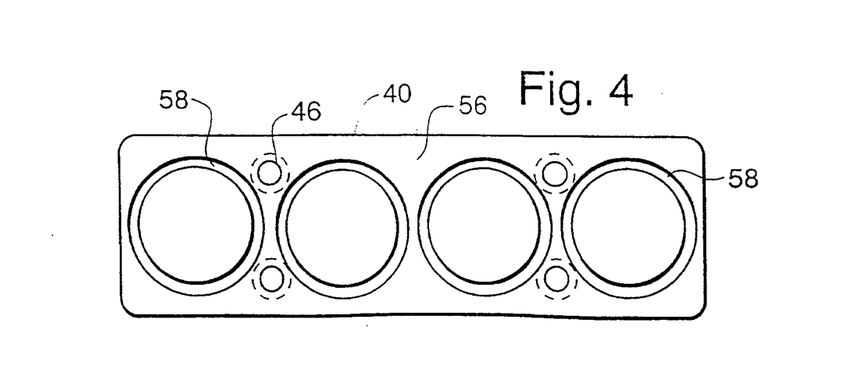
FIG. 4 is a bottom view of the holder cap.

As shown in FIG. 4, the bottom surface 56 of cap 40 is provided with at least one annular recess 58. The number of recesses 58 is preferably equal to the number of containers 34 which may be concurrently held by holder 18. This number is four in the illustrated embodiment. Each recess 58 accommodates an O-ring 88 (FIG. 9) to provide a seal as subsequently described.

FIGS. 5–8 show details of the holder body 42. The body 42 is provided with at least one bore 60, four bores 60 being shown in the Figures, extending through the body 42. Bores 60 are counter-bored from the surface 62 thereby forming inwardly projecting ledges 64 near an end of each bore 60. From ledges 64, the body 42 is flared outwardly at an angle, preferably measuring about 30°, thereby forming truncated generally cone-like surfaces 66. The flaring of the body 42 to form surfaces 66 serves two purposes. First, the surfaces 66 guide the containers 34 toward bores 60 as the holder 18 is moved with respect to the containers 34. Secondly, the surfaces 66 provide a wide mouth and thus a better angle for drilling a plurality of openings 68 in the side walls of bores 60.

As subsequently explained, the openings 68 form part of a fluid passage through which positive or negative pressures may be applied to the interior of bores 60 to inflate or deflate bladders 82 (FIGS. 9 and 10) disposed within the bores 60. Accordingly, the fluid passage is operatively connected with the bladders 82. The positive or negative pressures may be delivered through the fluid passage in the form of an appropriately pressurized fluid, such as air or other gas. An opening 68 is provided for interconnecting each adjacent pair of bores 60. To complete the fluid passage, a further opening 72 (FIG. 7) extends from one side of body 42 to the opening 68 connecting two adjacent bores 60. The opening 72 is preferably threaded and receives an elbow 74 (FIG. 1) having a flexible hollow tube 76 connected thereto.

The cap 40 and body 42 may be made from any suitable polymeric material, such as plastic and the like. By way of example only, the cap 40 may be made from a polymeric compound such as a substantially clear acrylic resin and the body 42 may be made of a polymer like white Delrin or white cast polyurethane.

Figure 9:
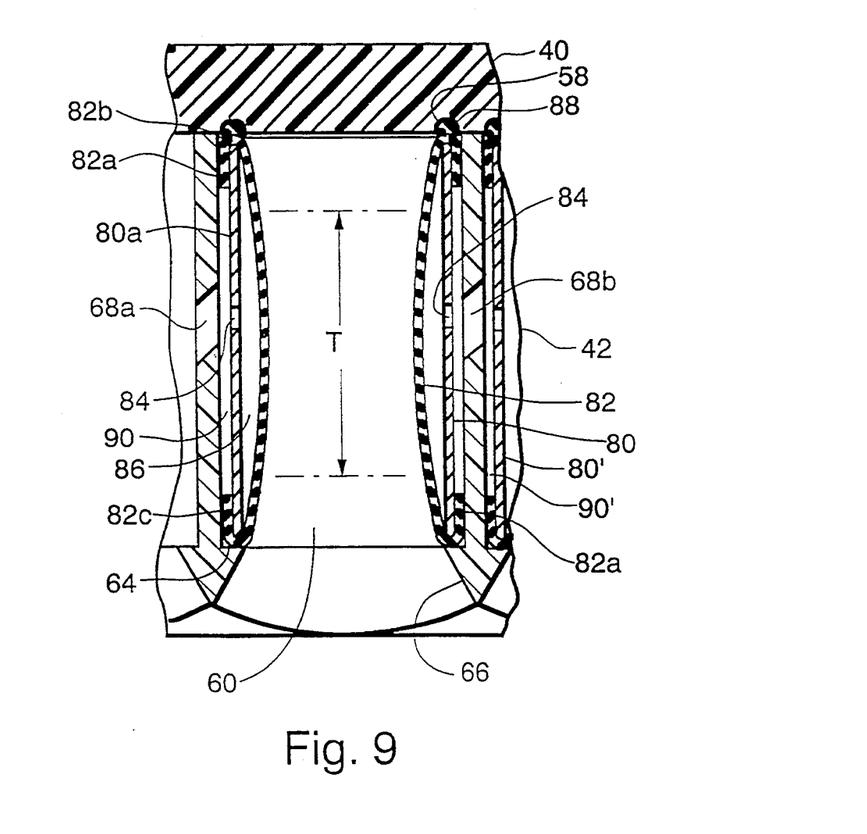
FIG. 9 is a sectional view of a part of the holder illustrating the gripper for one container and its cap.
Figure 10:
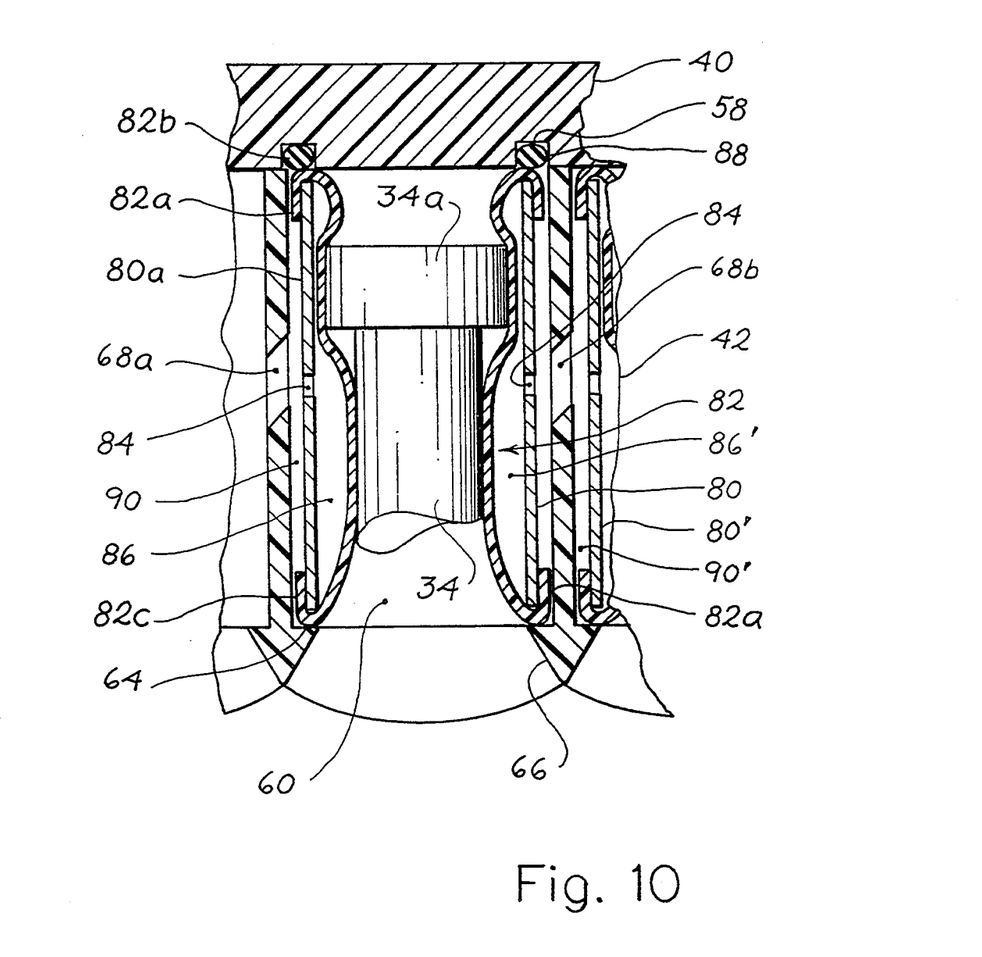
FIG. 10 is a view, similar to that of FIG. 9, showing the gripper applying a conforming cushioned compression to a container and its cap.

FIG. 9 is a sectional view of a portion of the holder 18 showing one of the bores 60. Mounted within the bore 60 is a first tubular element 80 and a second tubular or flexible element 82. Tubular element 80 is a rigid, preferably metal, cylinder having a plurality of bores 84 extending through its side wall. The tubular element 82 comprises a flexible, preferably silicone rubber, tube or bladder. In an exemplary embodiment, the tubular element 82 is made of an elastomeric material having sufficient elasticity such that at least a portion of the tubular element 82 can conform, as shown in FIG. 10, to a profile or external configuration of the container 34 and/or the cap 34a when the tubular element 82 sufficiently engages the container 34 and/or the cap 34a. This promotes retention of the container 34 within the bore 60 and retention of the cap 34a on the container 34.

In the illustrated embodiment, the flexible element 82 is longer than the rigid element 80 so that its ends 82a may be radially stretched and folded back over the outer surface 80a of the rigid element. The outer diameter of element 82 is preferably smaller than the inner diameter of element 80 so that when ends 82a are folded back a preferably air-tight, annular region or chamber 86 is formed between the elements 80 and 82. In a practical embodiment the diameter of the flexible element 82, before it is mounted on element 80, may be about ⅝" and the diameter of element 80 may be about ¾" although these dimension may be changed to accommodate container 34 of different sizes. At least one bore 84 in element 80 serves as a mechanism for allowing fluid movement into and out of the region 86. Preferably, at least four bores 84 are spaced around the periphery of element 84.

After the tubular elements 80 and 82 have been assembled, they are inserted into bore 60 from the top of body 42, as viewed in the Figures, after which the O-ring 88 is positioned on the body 42 and the cap 40 is secured to the body 42.

In the illustrated embodiment, the inner diameter of the flexible element 82 is chosen such that when the element 82 is folded back over the rigid element 80, the element 82 forms a throat region T whose largest diameter is preferably smaller than the diameter of the cap 34a and container 34 it is intended to grip. The diameter of the rigid element 80 is preferably smaller than the diameter of bore 60, but larger than the throat region T bounded by ledge 64, so that the ledge 64 supports elements 80 and 82 within bore 60. When the cap 40 is placed on body 42, the O-ring 88 presses against the tubular element 82 in the annular region 82b where it folds over an end of the rigid element 80 and this in turn presses an annular region 82c at another end of element 82 against ledge 64. An annular region or chamber 90, which is preferably hermetically sealed, is thus formed between the wall bounding bore 60 and the outer surface 80a of rigid element 80. The chamber 90 permits a fluid pressure present at one of the openings 68 to be communicated to the region 86 through all of the openings 84. The chamber 90 also permits a fluid pressure at a first opening 68a to be communicated to an adjacent chamber 90' through a second opening 68b.

During use of the sample container holder 18, positive and negative pressures are selectively applied to the chamber 86 where "positive" and "negative" are defined relative to the pressure of the ambient environment in which the holder 18 is being operated.

To provide the positive and negative pressures, the opening 72 (FIG. 7) is connected via flexible tubing 76 (FIG. 1) and two electrically controlled valves 92 and 94 to a source 96 of negative pressure and a source 98 of positive pressure. Pneumatic pressures are preferred although hydraulic pressures may be used. Thus, the pressurized fluid may also be a liquid. Controller 30 selectively produces output signals to open either valve 92 or 94, thereby applying a negative or a positive pressure via tube 76 to opening 72. From opening 72, the pressure is distributed via openings 68, regions 90 and bores 84 to the chamber 86.

As previously stated, in the preferred embodiment, the flexible element 82 is chosen to have, at ambient pressure in chamber 86, an internal diameter which is less than the diameter of a container 34 which is to be retained by the holder 18. The internal diameter of rigid element 80 is chosen such that when a vacuum or negative pressure is applied to chamber 86 to draw the flexible element 82 outwardly toward the internal surface of the rigid element 80, a sample container 34 and its cap 34a may move into the interior of the flexible element 82. The opening bounded by ledge 64 should preferably have a diameter larger than that of a sample container 34 and its cap 34a.

Referring now to FIGS. 1 and 9, the holder 18 is operated as follows. After a carrier 32 holding sample containers 34 is positioned adjacent holder 18, the controller 30 actuates valve 92 so that a negative pressure is applied via tube 76, bore 72 (FIG. 7), openings 68, regions 90 (FIG. 9) and bores 84 to chamber 86. The negative pressure in chambers 86 draws the flexible elements 82 toward the interior surfaces of rigid elements 80.

Next, controller 30 energizes the mechanism to move the mixer assembly 10. As the assembly 10 is moved, the caps 34a and upper portions of sample containers 34 are directed toward the interiors of the flexible element 82 by the sloping surfaces 66. Controller 30 then terminates the signal to valve 92 and energizes valve 94 so that a positive pressure is applied to the chambers 86. This pressure forces the flexible elements 82 away from the internal surfaces of rigid elements 80. As they move inwardly, the elements 82, because they are flexible, engage both the caps 34a and upper portions of the sample containers 34. The elements 82 engage the containers 34 and the caps 34a with a cushioned, conforming compression, as shown in FIG. 10, generated by pneumatic forces induced by the pressures. The cushioning, conforming compression also permits the holder 18 to receive and retain various containers 34 having variously different external configurations or profiles. The flexibility of the elements 82 combined with the pneumatic forces allows the elements 82 to assume a configuration which complements, mirrors or mates with the external configuration of the containers 34 and the caps 34a. This also reduces the probability that the caps 34a might separate from the containers 34 during the lifting and shaking operations which follow.

In an exemplary embodiment, the positive pressure applied to form the cushioned compression is about 2 to 5 psi. The maximum positive pressure is often dictated by the structural integrity of the container 34. Thus, it is to be noted that the maximum value of the positive pressure is predetermined to insure that the container 34 or the cap 34a will not be adversely effected by the application of the cushioned compression. The negative pressure, in the exemplary embodiment, is usually about 20 inches of mercury. The negative pressure value is predetermined to allow efficient intended movement of the container 34 and the cap 34a within the bore 60 while also not adversely effecting the construction of the holder 18.

The controller 30 next energizes the mechanism to move the holder 18 and the sample containers 34 until the sample containers 34 are free of the carrier 32. The controller 30 then energizes stepper motor 12 to shake the containers 34 by rotating them back and forth through an arc as described above. After the containers 34 have been shaken, controller 30 energizes the mechanism for moving the mixer assembly 10. As the assembly 10 is moved, portions of sample containers 34 are again received into the receptacles 36 in carrier 32.

The controller 30 now deenergizes valve 94 and energizes valve 92 to again apply a negative pressure to the chambers 86. This draws the flexible elements 82 away from the containers 34 and the containers 34 move into the carrier 32. This movement may be gravity assisted.

Alternatively, an ejector of sorts may be provided. With valve 92 still energized, the controller 30 energizes the mechanism for moving the mixer assembly 10. As the holder 18 is moved, the flexible elements 82 move relative to the sample containers 34. This movement is relatively free because the pneumatic forces have been relaxed. The mixing cycle is complete once the holder 18 has been sufficiently offset from the containers 34. Once the holder 18 is offset from the containers 34 sufficiently, a new container carrier 32 may be moved into position adjacent holder 18.

Put in another way, the method of using the sample container holder 18 may be considered as comprising the steps of receiving the sample container 34 within the bore 60 in the body 42 of the sample container holder 18 and introducing a pressure through the fluid passage toward the chambers 90, 90" and regions 86, 86' to change the inner diameter of the second flexible element 82 to retain the container 34 and the cap 34a within the bore 60.

The embodiments of the present invention provide distinct advantages over the prior art. According to the above-discussed methods, the holder 18 operates in a fail-safe mode which can reduce the chances of dropping a sample container 34 in the event of a power loss or other failures. Since the internal diameter of flexible elements 82 is less than the diameter of the sample containers 34 when ambient pressure is present in chambers 86, the elements 82 will still grip the containers 34 even when positive pressure is lost because of a power or other component failure. The holder 18 will retain a container 34 as long as the pneumatic forces generating the cushioning compression on the container 34 and the cap 34a are of sufficient magnitude to resist a force directed to remove the container 34 from the holder 18, or, more precisely, from the bore 60 in the holder 18. As long as the cushioning compression applied to the container 34 or the cap 34a, or both is of the sufficient magnitude, the container 34 will remain with the holder 18.

Because these methods accomplish gripping of the containers 34 by moving flexible elements 82 with a pneumatic pressure, the holder 18 is able to grip containers 34 and their caps 34a even though the diameters of the containers 34 and the designs of their caps 34a may vary. This is a direct benefit of the conforming cushioning compression applied to the container 34 and the cap 34a by flexible elements 82 operated according to the above-described methods.

From the foregoing description it is seen that the embodiments of the present invention provide methods for operating a sample container holder which are able to accommodate sample containers of various sizes while using a single holder, reduce the chances of separating containers from their caps, and reduce the chance of dropping containers in the event of a power loss or other failure.

While preferred embodiments of the invention have been described in specific detail it will be understood that various modifications and substitutions may be made in the described embodiments without departing from the spirit and scope of the appended claims. Container holders other than the holder 18 may also be used with the above-discussed methods. Furthermore, although the sample container holder and methods of its use have been described in the environment of a mixer device, it should be understood that the holder and associated methods may find general utility in transferring sample containers from carriers to analytical devices, from one stage to another of a multi-stage analytical device, etc.

I claim:

1. A method of holding a sample container that contains a sample with a sample container holder, the method comprising the steps of:
   (a) providing a sample container holder comprising a body having at least one bore in which i, a sample container is received, first and second tubular elements disposed within the at least one bore, the first tubular element being rigid, the second tubular element being flexible and disposed within the first tubular element with first and second ends of the second tubular element being folded back over first and second ends of the first tubular element so as to form a substantially sealed chamber between the first and second tubular elements; and the first tubular element and the body having an opening therein comprising a fluid passage operatively connected with the chamber;
   (b) receiving a sample container within the at least one bore in the body of the sample container holder; and
   (c) introducing a pressure through the fluid passage to the chamber to move the second tubular element in contact with the sample container for retaining the sample container in the at least one bore in the body of the sample container holder.

2. A method as defined in claim 1 wherein the introducing step (c) comprises introducing a negative pressure to offset the second tubular element from the sample container.

3. A method as defined in claim 1 wherein the introducing step (c) comprises introducing a positive pressure so that the second tubular element applies a cushioning compression to the sample container.

4. A method as defined in claim 1 wherein the introducing step (c) comprises introducing a positive pressure so that the second tubular element conforms to a profile of the sample container.

5. A method as defined in claim 1 wherein the introducing step (c) comprises introducing an ambient pressure so that the sample container is retained by the second tubular element within the at least one bore.

6. A method of holding a sample container with a sample container holder, the method comprising the steps of:
   (a) locating a flexible element within a bore in a body comprising the sample container holder;
   (b) operatively connecting the flexible element with a fluid passage in the body;
   (c) drawing the flexible element toward an interior surface of the bore;
   (d) guiding the sample container within the bore in the body;
   (e) supplying a fluid to the flexible element through the fluid passage;
   (f) moving the flexible element away from the interior surface of the bore;
   (g) engaging the sample container with the flexible element to form a conforming cushioning compression between the flexible element and the sample container; and
   (h) resisting removal of the sample container from the bore.

7. A method as defined in claim 6 wherein the engaging step (g) comprises engaging the flexible element and the sample container with a pressure of about 2 psi. to about 5 psi.

8. A method as defined in claim 6 wherein the drawing step (c) comprises applying a negative pressure of about 20 inches of mercury to the flexible element.

9. A method as defined in claim 6 further comprising the step of:
(i) shaking the sample container with the sample container holder.

10. A method as defined in claim 9 wherein the shaking step (i) comprises rotating the sample container with the sample container holder back and forth through an arc.

11. A method as defined in claim 6 further comprising the step of:
(i) removing the sample container from the sample container holder.

* * * * *